United States Patent [19]
Nakamura et al.

[11] Patent Number: 5,930,328
[45] Date of Patent: *Jul. 27, 1999

[54] X-RAY EXAMINATION APPARATUS HAVING AN AUTOMATIC POSITIONING SYSTEM FOR AN IMAGING SYSTEM

[75] Inventors: Masato Nakamura; Naobumi Ishikawa, both of Tochigi-ken, Japan

[73] Assignee: Kabushiki Kaisha Toshiba, Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/736,060

[22] Filed: Oct. 22, 1996

[30] Foreign Application Priority Data

Oct. 27, 1995 [JP] Japan .............................. P07-281059

[51] Int. Cl.$^6$ ........................................ H05G 1/08

[52] U.S. Cl. .................................... 378/91; 378/115

[58] Field of Search .............. 378/91, 115, 116

[56] References Cited

U.S. PATENT DOCUMENTS

| 4,807,273 | 2/1989 | Haendle | 378/116 |
| 5,023,899 | 6/1991 | Ohlson | 378/91 |

*Primary Examiner*—Craig E. Church
*Attorney, Agent, or Firm*—Oblon, Spivak, McClelland, Maier & Neustadt, P.C.

[57] ABSTRACT

A versatile X-ray examination apparatus including a movable table top for supporting a patient, an imaging system having an X-ray source adopted for passing X-rays through the patient and an image receptor for generating an X-ray image of the patient, the image receptor is automatically moved to a desired position by a control system. The control system includes a memory for storing data concerning the table top, a control circuit for detecting a plurality of moving amounts of a plurality support members for supporting the imaging system, and a moving amount calculator for calculating a moving amount of the image receptor along a radiation axis on the basis of the data in the memory and the detected moving amount data provided from the control circuit.

19 Claims, 6 Drawing Sheets

X-RAY EXAMINATION APPARATUS HAVING AN AUTOMATIC POSITIONING SYSTEM FOR AN IMAGING SYSTEM

BACKGROUND OF THE INVENTION

1. Field of the Invention

The present invention relates to an X-ray examination apparatus including a movable table top system and a surrounding X-ray imaging system, both of which are movable by the combined movements of a plurality of carriage means supporting the X-ray imaging system.

In particular, the present invention relates to an X-ray examination apparatus which includes an automatic positioning system for moving an image receptor in the X-ray imaging system along a radiation axis of the X-ray by interlocking the carriage means.

More particularly, the present invention relates to a versatile X-ray examination apparatus which can automatically change between an automatic positioning mode and a manual positioning mode of the image receptor in the imaging system in response to a location of the image receptor against a table top.

2. Discussion of the Background

X-ray examination apparatuses are used both in medicine and industry. In order to simplify the description of the apparatus, the discussion below is directed only toward medical applications.

The X-ray examination apparatus includes a movable table top for supporting a patient being examined and an X-ray source and an imaging receptor mounted on opposite ends of a C- or U-arm carriage means (hereinafter "C-arm") so as to surround the table top.

Usually, an image intensifier (hereinafter "I.I.") is used as the image receptor for detecting X-rays transmitted through a patient'body and for reproducing X-ray images. In a versatile X-ray examination apparatus, the reproduced X-ray images are usually displayed on a monitor, such as a television monitor.

Depending upon the purpose of a diagnostic examination, the radiation axis of the X-ray examination apparatus must be moved in various directions in order to obtain a plurality of X-ray images by intersecting the patient's body in various directions. Changing the intersecting directions is required, in particular, when a contrast medium, such as barium, is used during the examination.

In a conventional X-ray examination apparatus, a patient is required to change his posture in various directions by himself in order to move the contrast medium to a desired position in his body. Moving on the table top is often difficult for elderly or disabled patients.

A versatile X-ray examination apparatus has been developed for avoiding these difficulties for patients. In the versatile X-ray examination apparatus, a patient is supported on a table top and does not move with respect to the table top as both the table top and the imaging system are moved in various directions. The imaging system usually includes an X-ray source and an image receptor which are mounted on opposite ends of a C-arm holder so as to dispose the table top between them.

By combining the respective movements of the table top and the C-arm holder, the versatile X-ray examination apparatus can obtain various X-ray images of the patient's body in various directions without any difficulties for the patient.

However, it is very difficult to manually move the image receptor as close as possible to the patient's body or the table top by interlocking the movements of the table top and the carriage means for the imaging system. Such a manual positioning of the image receptor at a specified closest position to the table top is very important for obtaining a good quality reproduced X-ray image.

It is very difficult to move the image receptor to the best position by a manual operation because the operator sometimes cannot see the position of a detecting surface of the I.I. from his position at a control panel due to the position of the table top or the patient's body. In such a case, the operator is obliged to move the I.I. while estimating the best position.

Some of the I.I.s in conventional versatile X-ray examination apparatuses have touch sensors on the detecting surface for automatically stopping the movement of the I.I. when the detecting surface touches a surface of the table top or the patient body. Even in the versatile X-ray apparatus, the I.I. must be manually moved in a reverse direction after stopping for backing the I.I. to a desired position for obtaining the best magnification of a reproduced X-ray image.

As mentioned above, it is very difficult to place the detecting surface of the I.I. in the conventional versatile X-ray examination apparatus at the best position for obtaining a desired magnification of the X-ray image. Further, the manual operation for positioning the I.I. at a desired position is a time consuming one. Consequently, a patient may feel stressed or fatigued during the preparation time before the actual examination.

SUMMARY OF THE INVENTION

Accordingly, one object of the present invention is to solve the above-mentioned problems and defects of the conventional versatile X-ray examination apparatus.

Another object of the present invention is to provide a novel X-ray examination apparatus which can automatically place the I.I. at a required position by interlocking the movements of the table top and the imaging system.

A further object of the present invention is to provide a novel versatile X-ray examination apparatus which can automatically move the I.I. with respect to the C-arm movements by a real time calculation for determining the amount of movement in response to the respective movements of the C-arm carriage means.

A still further object of the present invention is to provide a novel versatile X-ray examination apparatus which includes an automatic positioning system for positioning the I.I. at a desired position by a faster operation than that performed by the conventional versatile X-ray examination systems.

These and other objects are achieved according to the present invention by providing a novel versatile X-ray examination apparatus including a table top for supporting a patient being examined; an X-ray source for irradiating the patient with X-rays while on the table top; an image receptor for generating an X-ray image of the patient by detecting X-rays transmitted through the patient's body; a support means for mounting the X-ray source and the image receptor on opposite ends so as to dispose the table top between them, where the X-ray source and the image receptor have a common radiation axis which rotates around the table top in accordance with movements of the support means; a plurality of carriage means for holding and moving the support means, where the carriage means are coupled with each other so as to move the X-ray source and the image receptor in various directions by combining the independent movements of the respective support means; and a control system for decoding the movement of the image receptor along the common radiation axis by calculating the movement of the respective support means, thus obtaining the required magnification of the X-ray image.

BRIEF DESCRIPTION OF THE DRAWINGS

A more complete appreciation of the present invention and many of the attendant advantages thereof will be obtained by reference to the following detailed description when considered in connection with the accompanying drawings, wherein.

DESCRIPTION OF THE PREFERRED EMBODIMENTS

Figure 4:
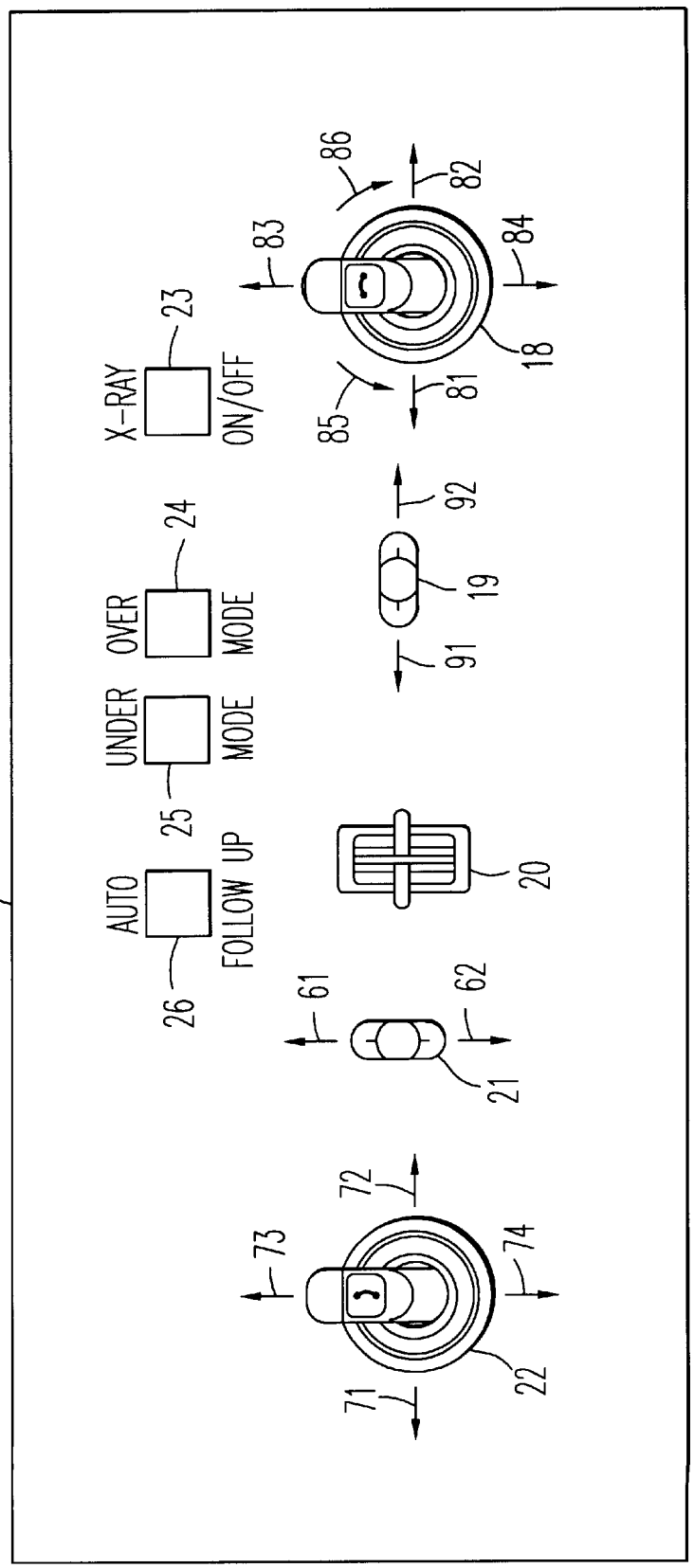
FIG. 4 is an example of a control panel for using in the versatile X-ray examination apparatus of the present invention shown in FIG. 1.
Figure 5:
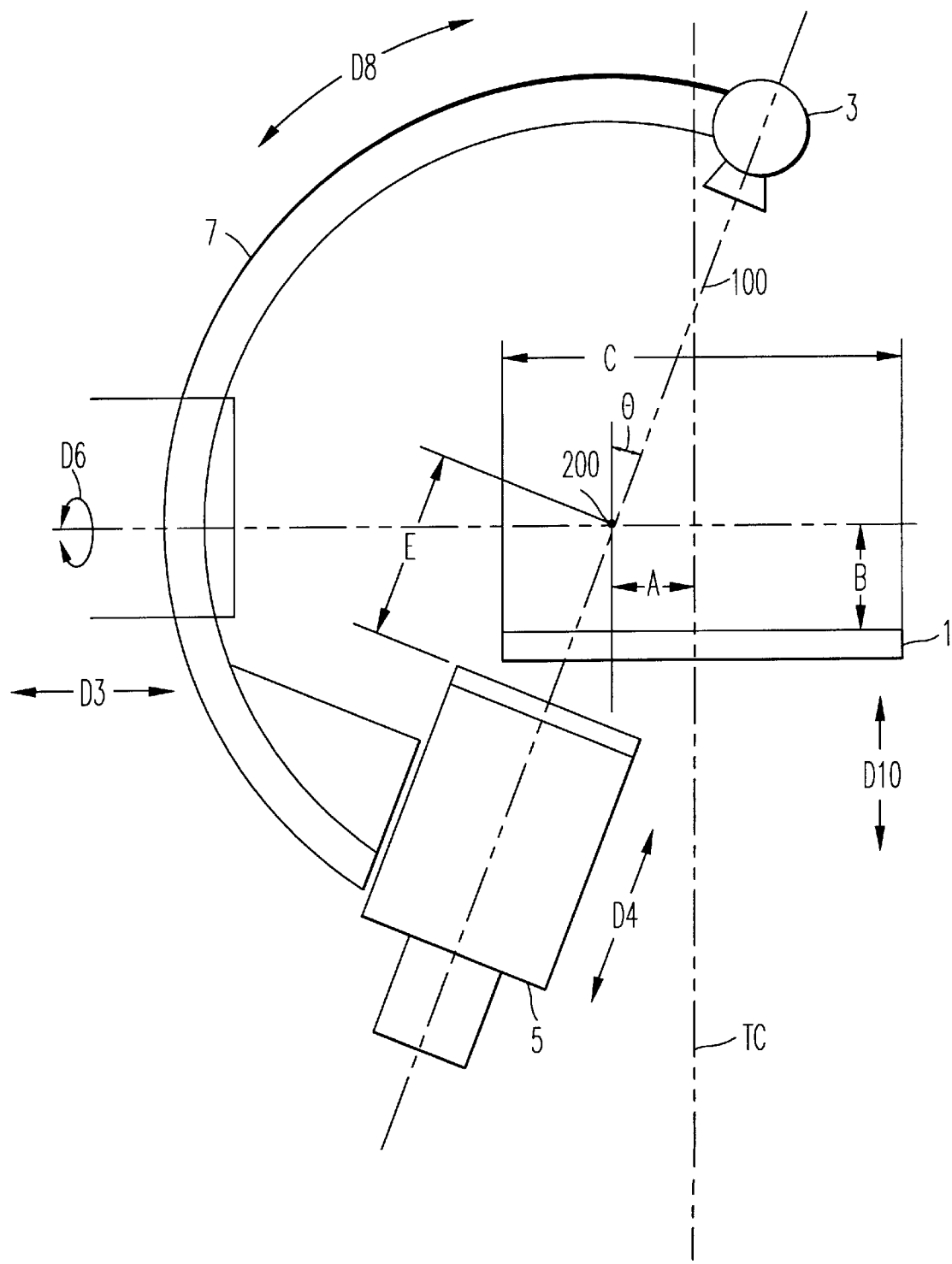
FIG. 5 is a simplified view demonstrating the alignment of the X-ray imaging system including a X-ray source and an image receptor and the table top.
Figure 6:
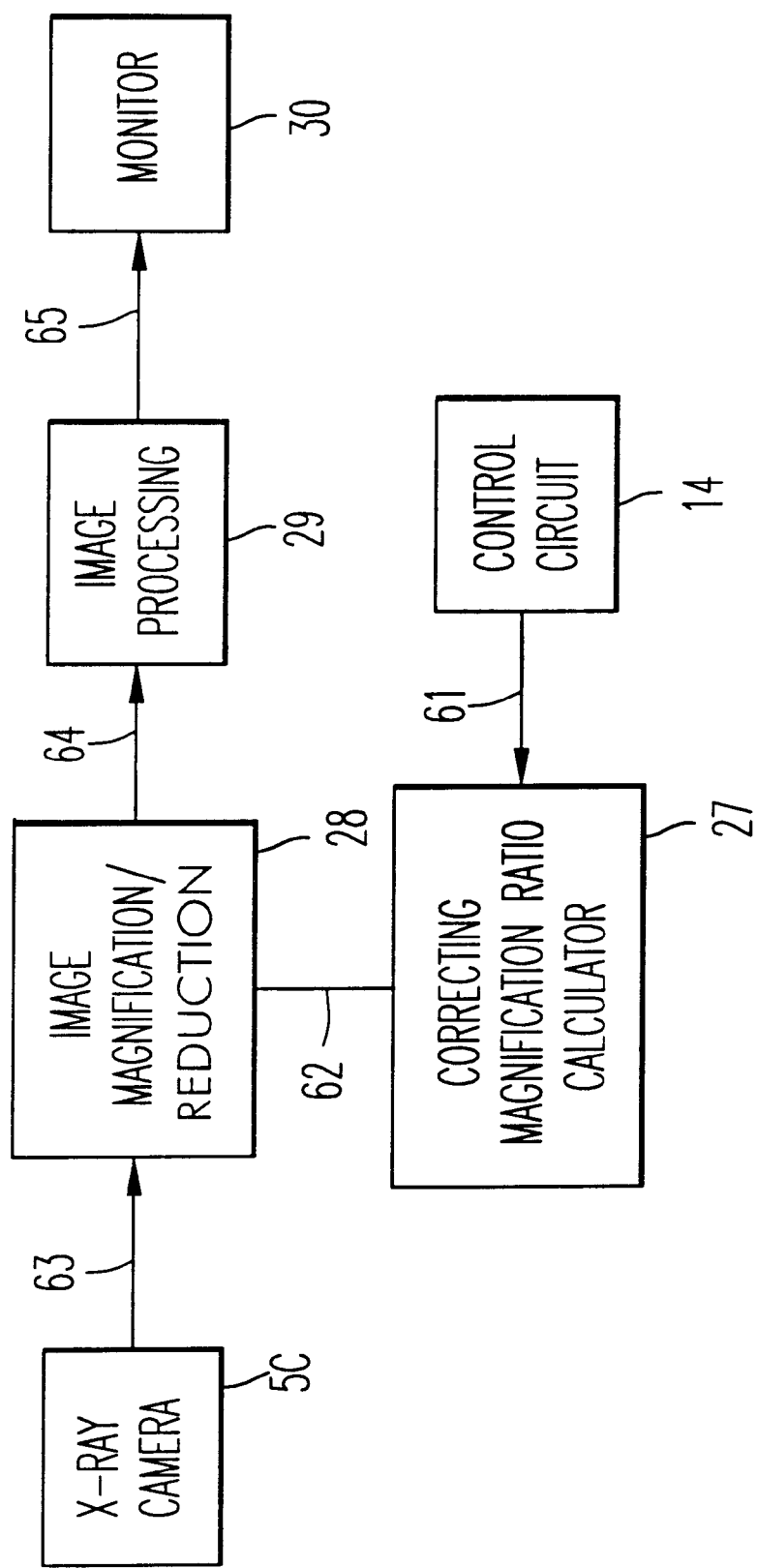
FIG. 6 is a block diagram demonstrating an example of an image processing system of the versatile X-ray examination apparatus according to the present invention.

A versatile X-ray examination apparatus according to the present invention is illustrated in one embodiment in the drawings of FIGS. 1 to 5 and in an image processing system in the drawing of FIG. 6.

In the figures, the respective movements of the components of the X-ray examination apparatus which comprises a table top, a C-arm holder, and a plurality of carriage means for the C-arm holder are shown by arrows which are defined as follows:

1) d1—a rolling movement of a table top around a longitudinal center axis of the table top;
2) d2—an up-and-down movement of a table top parallel to a floor;
3) d3—a back-and-forth movement of the table top orthogonally crossing a longitudinal axis of the table top and in parallel to a floor;
4) d4—an up-and-down movement of an image receptor against the table top;
5) d5—a pitching movement of a carriage base for supporting a frame carriage;
6) d6—a pitching movement of a support frame support;
7) d7—a longitudinal movement of a frame carriage in parallel to the longitudinal center axis of the table top;
8) d8—a rolling movement of a C-arm holder;
9) d9—an up-and-down movement of a X-ray source against the table top; and
10) d10—an up-and-down movement of a holder support.

Figure 1:
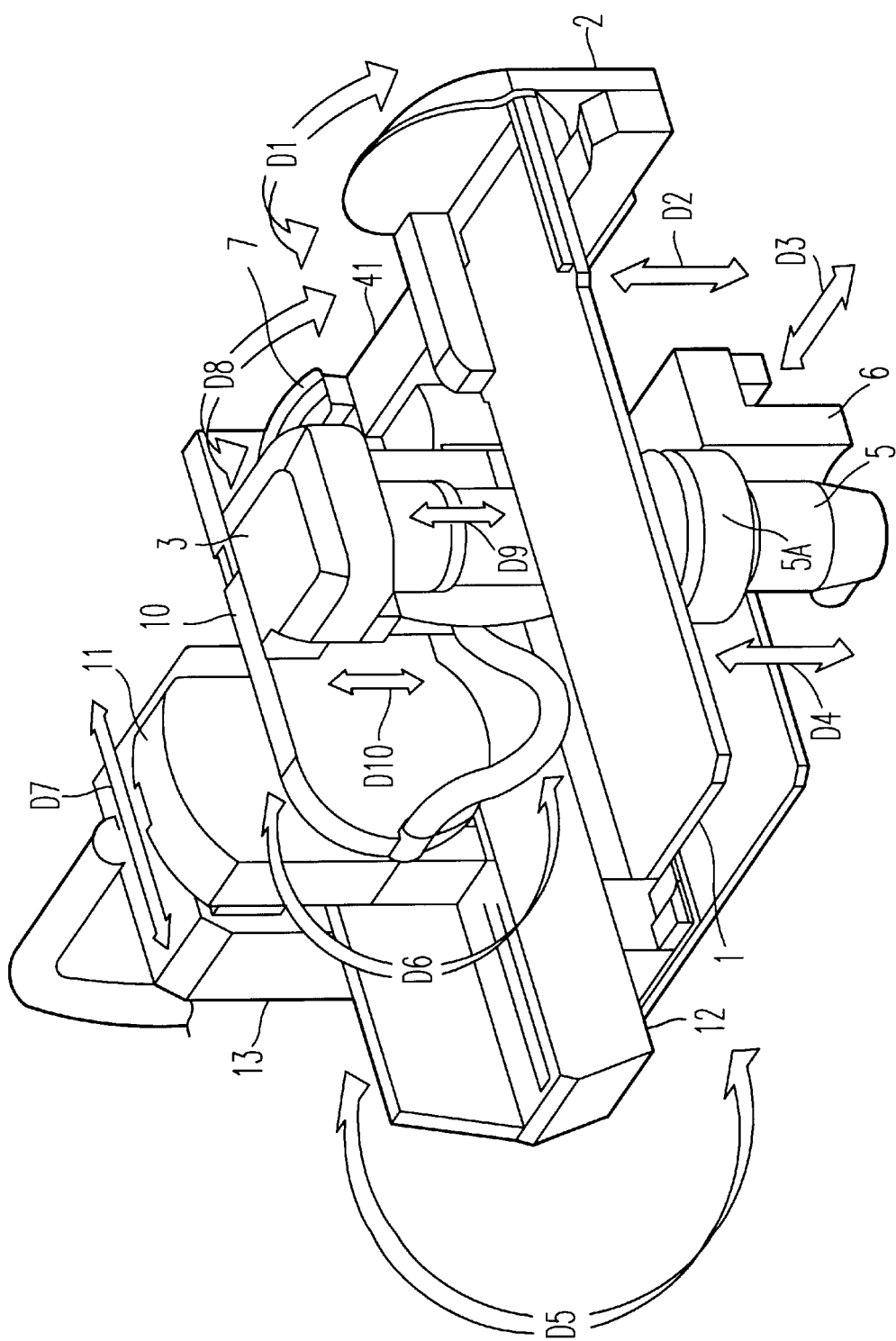
FIG. 1 is a perspective view of an embodiment of the versatile X-ray examination apparatus according to the present invention.
Figure 2:
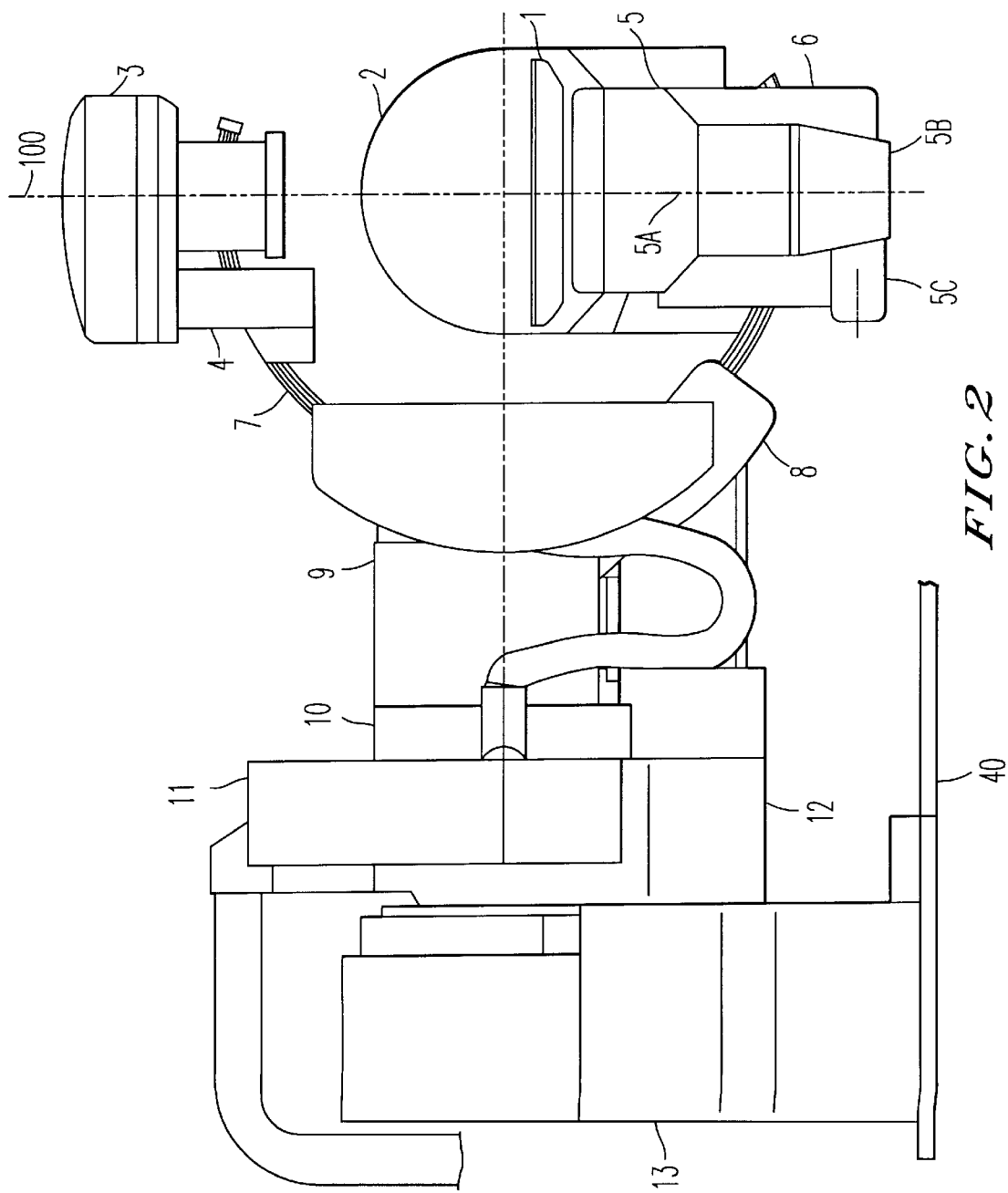
FIG. 2 is a side view of the embodiment of the versatile X-ray examination apparatus of the present invention shown in FIG. 1.

In FIGS. 1 and 2, a table top I comprising an X-ray permeable material, such as a carbon fiber reinforced plastic (CFRP), is mounted at one end in an overhanging arrangement by a table top support frame 2 so as to be disposed in between an X-ray source 3 and an X-ray image receptor 5. The table top support frame 2 includes a table top motion actuator 2a (not shown) which makes the table top move around a longitudinal axis of the table top as shown by the arrow d1.

The X-ray source 3 includes an X-ray tube and a focusing means for controlling a radiation field from the X-ray tube. The X-ray source 3 is supported by an X-ray source holder 4 which includes an X-ray source moving actuator 4a (not shown) for moving the X-ray source 3 in the direction d9.

As shown in FIG. 2, the X-ray source can move up and down along a radiation axis 100, thus moving the X-ray source toward or away from the table top. The radiation axis is defined by a common center axis for the X-ray source 3 and the X-ray imaging system 5.

The X-ray imaging system 5 includes an image intensifier (an "I.I." as defined previously) 5a as an image receptor, an optical system 5b and a camera 5c. The I.I. 5a converts the X-rays which pass through a patient's body on the table top 1 to an optical image. The optical system 5b transfers the converted optical image to the camera 5c. The camera 5c produces image signals in accordance with the optical image and send them to an image processing circuit for displaying reproduced images on a monitor.

The X-ray imaging system 5 is supported on an I.I. holder 6 which includes an I.I. moving actuator 6a (not shown) for moving the I.I. 5a in the up-and-down direction d4. The I.I. can be moved along the radiation axis 100, thus moving the I.I. toward or away from the table top.

The X-ray source holder 4 and the I.I. holder 6 are mounted on opposite ends of a C-shaped or U-shaped frame 7 (a "C-arm," as defined previously) so as to interpose the table top 1. The C-arm 7 is supported on a C-arm holder 8 which includes a C-arm rotating actuator 8a (not shown) for rotating the common radiation axis 100, which is an imaginary line passing through the center of the X-ray source 3 and the center of the I.I. 5a.

The X-ray source and the I.I. can be rotated around the table top 1 along the path denoted d8.

The moving direction d3 of the table top 1 orthogonally intersects a center axis a corresponding to the movement of the C-arm 7.

The table top support 2 is mounted on a connecting frame 41 which is fixed to one end portion of a lateral base frame 12. The table top 1 moves by interlocking it to the pitching movement of the lateral base frame 12.

The C-arm holder 8 is supported on a holder support 9 which includes a C-arm holder moving actuator 9a (not shown) for moving the C-arm holder 8 in parallel to the floor 40 in the back-and-forth direction d3.

The holder support 9 is mounted on a frame carriage 10. In the frame carriage 10, a frame carriage moving actuator 10a (not shown) is provided for moving the holder support 9 both along the path denoted d6 and in the up-and-down direction d10. The X-ray source 3 and the I.I. 5a rotate around a second C-arm rotation center axis β coordinated with the pitch of the holder support 9.

The second C-arm rotation center axis β orthogonally intersects the first C-arm rotation center axis α. The intersecting point of the first and second rotation center axes α and β is referred to as a C-arm center 200, as depicted in FIG. 5.

The frame carriage 10 is supported on a carriage base 11 which includes a frame carriage moving actuator 11a (not shown) for moving the frame carriage 10 in the up-and-down moving direction d10.

The carriage base 11 is mounted on a lateral base frame 12. As mentioned before, the table top support 2 is coupled to the lateral base frame 12 through the support frame 41 for rotating the table top 1 along the path denoted d5.

The lateral base frame 12 includes a carriage base moving actuator 12a (not shown) for sliding the carriage frame 11 on the base frame 12 in the lateral direction d7. The lateral base frame 12 is supported on a base stand 13 which is engaged to the floor 40 in an examination room.

The base stand 13 includes a first actuator 13a (not shown) for rotating the lateral base frame 12 along the path denoted d5 and a second actuator 13b (not shown) for moving the lateral base frame 12 in the up-and-down direction d2.

By combining the movements of these plurality of actuators for the respective frames, universal movement of the C-arm can be achieved which depends upon the purpose of the examination.

The actuators 2a, 4a, 6a, 8a–13a, and 13b include sensors for detecting linear or angular motion by the particular actuator. The motion indicates an absolute position for each actuator.

One of the characteristic features of the X-ray examination apparatus according to the present invention is to automatically calculate the moving amount for the I.I. actuator 6a in accordance with the combined movements of the plurality of C-arm holders in an automatic positioning mode of operation.

The movement control system for the versatile X-ray examination apparatus according to the present invention is explained with reference to FIGS. 3 and 4.

Figure 3:
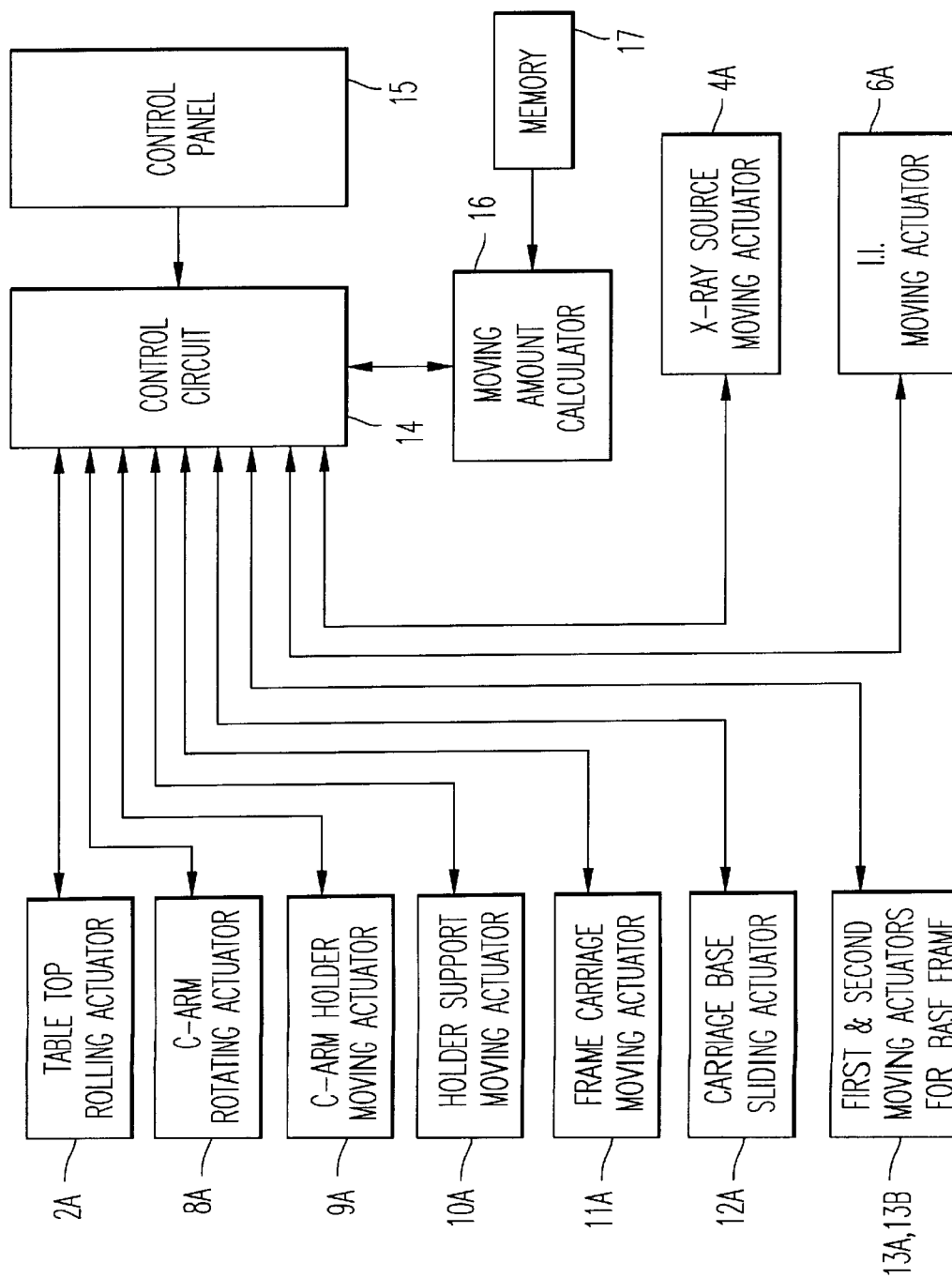
FIG. 3 is a block diagram showing an embodiment of the control system for automatically moving various devices in the versatile X-ray examination apparatus of the present invention shown in FIG. 1.

As shown in FIG. 3, the movement control system for the versatile X-ray examination apparatus according to the present invention includes a control circuit 14, a control panel 15, a moving amount calculator 16 and a memory 17 for storing size data for the table top and the patient.

The control panel 15 provides a plurality of moving signals to the respective actuators. It also indicates entering the automatic positioning mode of operation for the I.I.

The moving amount of the I.I. during the automatic positioning mode of operation is decided by the moving amount calculator 16 on the basis of the moving amount data through the control circuit 14 and the memory 17. The actuators 2a, 4a, 8a–13a, and 13b provide the data for the particular linear or angular motion to the control circuit 14.

The memory 17 stores data for representing the shape and size of the table top, data for the average size of a patient and data for the shape and scale of the radiation surface of the X-ray source.

The control panel 15 directs the movement of the various actuators through the control circuit 14 by the manual operation of handles or switches on the panel, such as those shown in FIG. 4.

In FIG. 4, a first handle lever 18 instructs the rotating movement of the table top and the movement of the C-arm. When the lever 18 is horizontally moved as indicated by arrows 81 and 82, the control circuit 14 provides a moving instruction to the C-arm holder moving actuator 9a for moving the C-arm in the direction d3. When the lever 18 is vertically moved as indicated by arrows 83 and 84, the control circuit 14 provides a movement instruction to carriage base sliding actuator 12a for moving the C-arm in the direction d7.

When the lever 18 is twisted as indicated by arrows 85 and 86, the control circuit 14 provides a moving instruction to the table top rolling actuator 2a for rotating the table top in the path denoted d1.

A second lever 19 is used for manually instructing the movement of the lateral base frame 12. When the lever 19 is horizontally moved as indicated by arrows 91 and 92, the control circuit 14 provides a moving instruction to the first and second moving actuators 13a and 13b for moving the base frame 12 along the path denoted d5 and in the up-and-down direction d10.

The focusing lever 20 controls the X-ray radiation area from the X-ray source. By moving the lever 20 vertically, the radiation area can be changed depending upon the purpose of the examination.

A second handle lever 22 instructs the rotation of the C-arm. When the lever 22 is horizontally moved as indicated by arrows 71 and 72, the control circuit 14 provides a moving instruction to the frame carriage moving actuator 11a for rotating the C-arm along the path denoted d8 around the first C-arm rotating center axis α.

When the lever 22 is vertically moved as indicated by arrows 73 and 74, the control circuit 14 provides a moving instruction to the C-arm rotating actuator 8a for rotating the C-arm around the second C-arm rotating center axis β.

The control panel 15 further includes an X-ray radioscopy on/off switch 23, an over-table-tube mode switch 24, an under-table-tube mode switch 25 and an I.I. automatic positioning switch 25.

The X-ray radioscopy on/off switch 23 controls X-ray radiation from the X-ray source during the examination. During radioscopy, switch 23 turns on, the X-ray source radiates X-rays to a patient's body being examined, and the X-ray radiation passed through the patient's body is detected and reproduced as an X-ray image by the X-ray imaging processing system. The reproduced images are displayed on a monitor.

When the over-table-tube mode switch 24 is turned on, the X-ray source emits radiation from the upper portion of the table top. Turning on the under-table-tube mode switch 25 causes the X-ray source to emit radiation from under the table top. When the under-table-tube mode 25 is turned on, the radiation direction is changed by rotating the pair of the X-ray source and the I.I. around the second C-arm rotating center axis β. Then the X-ray source is disposed under the table top.

When the over-table-tube mode switch 24 is turned on, the control circuit 14 issues an instruction to enter an I.I. automatic positioning mode. On the contrary, when the undertable-tube mode switch 25 is turned on, the control circuit 14 issues an instruction to release from the I.I. automatic positioning mode.

During the rotation of the C-arm caused by changing between the over-table-tube mode and the under-table-tube mode, the control circuit 14 directs the movement of the plurality of actuators so as to rotate the X-ray source and the I.I. without touching any of the moving actuators.

The automatic positioning switch 26 can manually instruct the control circuit 14 for entering into or releasing from the I.I. automatic positioning mode.

An I.I. moving switch 21 controls a manual movement of the I.I. By vertically sliding the switch 21 as indicated by arrows 61 and 62, the I.I. can be moved along the common axis 100. When the switch 21 is operated, the control circuit 14 releases the I.I. from automatic positioning mode.

One of the key features of the X-ray examination apparatus according to the present invention is the I.I. automatic positioning mode. During the I.I. automatic positioning mode, the control circuit 14 controls the I.I.'s movement along the common radiation axis 100 by the calculating result from the calculator 16.

Namely, the moving amount of the I.I. along the radiation axis is decided by the calculation based on the movements of the actuators other than the I.I. moving actuator. By the automatic movement, it is possible to approach the table top with the I.I. so that the I.I. is as close as possible to the table top without actually touching it.

The calculation for deciding the moving amount of the I.I. is achieved by using the movements of the various actuators as the calculation parameters.

The parameters used for the calculation are the rotating angle of the table top rolling actuator 2a and the C-arm rotating actuator 8a and the movements of the holder support moving actuator 10a, the C-arm holder moving actuator 9a, and the frame carriage moving actuator.

Further, the calculation is made by using the stored data regarding the size of the table top and of the patient being examined in the memory 17.

The size data of the table top, for example, comprise a lateral length c and a thickness of the table top 1. A patient body is approximated by an ellipse. Accordingly, the size data of the patient being examined are long and short axes of the approximated ellipse.

It is possible to select the size data from a plurality of data which are previously stored in the memory by using a selection switch means.

Further, it is possible to use combined data of the table top size and the patient body size for the calculation. Of course, at this time, the combined data also are stored in the memory 17 in the combined form.

Another key feature of the X-ray examination apparatus according to the present invention is that the calculator 16 makes the calculation of the I.I. moving amount in real time following the combined movements of the plurality of the C-arm holding devices. Namely, during the automatic positioning mode, the control circuit 14 drives the I.I. moving actuator 6a in accordance with the movement determined by the real time calculation the movement of the respective C-arm holding device.

FIG. 5 is a simplified view for describing the calculation in the X-ray examination apparatus according to the present invention. In FIG. 5, the table top 1 moves in parallel to the back-and-forth direction d3. The C-arm 7 rotates around the rotation center axis a along the rotating direction d8. The inclination angle θ of the common radiation center axis is between +90° and −90°.

Under this condition, the moving distance E of the detecting surface of the I.I. 5 from the C-arm center 200 is decided by equation (1), $$E = f(a, b, \theta) \quad (1)$$
$$= -a \cdot \sin\theta + b \cdot \cos\theta + \frac{c}{2} \cdot |\sin\theta| + d,$$

where a is a distance between the C-arm center 200 and the lateral center of the table top 1. The distance a is obtained from the moving amount of the C-arm holder moving actuator 8a. The measurement b is the vertical distance between the surface of the table top 1 and the C-arm rotation axis β which passes through the C-arm center 200 and is obtained from the moving amount by the frame carriage moving actuator 11a. The measurement c is a lateral width of the table top 1 and is previously stored in the memory 17. The measurement d is a previously decided margin. The angle θ is obtained from the sliding angle by the C-arm rotating actuator 8a.

By using the moving distance E which is obtained by equation (1), the moving amount of the I.I. moving actuator 6a is obtained.

The conversions from the moving amount of the respective actuators to the corresponding variables a, b, c, d and θ are made by using a conversion table which is stored in the memory 17. It is also possible to convert the moving amount to the variable by a calculation using the data which indicates the respective configurations of the C-arm holding devices.

If the table top 1 varies along the longitudinal detection, the moving amount E of the I.I. moving actuator 6a is obtained by adding the moving amount of the carriage base sliding actuator 12a to the result of equation (1).

The above-mentioned calculation is made under the assumption that the width of the imaging field of the X-ray source is unlimited. This assumption suffers no difficulties in the actual use of the X-ray examination apparatus. However, it is also possible to use the width of the imaging field of the X-ray source as a limiting parameter for the calculation in order to increase the precision of the calculation.

As explained above, the I.I. 5 in the X-ray examination apparatus of the present invention can automatically move against the C-arm 7 in response to the movements of the plurality of the C-arm holder devices. Consequently, the apparatus can eliminate the complicated and the time consuming positioning of the I.I. in the conventional apparatus.

This automatic positioning mode of the I.I. during the over-table-tube mode is automatically released when the under-table-tube mode is selected so that there is no possibility of malfunction during the manual adjustment of the I.I. position in the X-ray examination apparatus of the present invention.

When the I.I. 5 is moved against the C-arm 7, the magnification of the detected X-ray image also changes due to a variation between a focusing point of the X-ray source 3 and an image detecting surface of the image receptor 5. The distance between the focusing point of the X-ray source 3 and the image detecting surface of the image receptor 5 is referred to as an "SID."

FIG. 6 is a block diagram of an X-ray image displaying system for correcting the variation of the reproduced X-ray image magnification.

The control circuit 14 provides a data signal 61 relating to the moving amount of the I.I. to a correcting magnification ratio calculator 27. The calculator 27 provides a correcting magnification ratio in response to the movement of the I.I. entered into one input terminal of an image magnification/reduction circuit 28.

The X-ray camera 5c in the X-ray imaging system provides X-ray image signals 63 to a second input terminal of the image magnification/reduction circuit 28. The circuit 28 magnifies or reduces the X-ray image in accordance with the instructed ratio.

The magnified or reduced X-images 64 are processed in an image processing circuit 29 and the processed images 65 are displayed on a monitor 30. The image processing includes, for example, subtraction.

The image magnification/reduction ratio for maintaining a constant image magnification is decided by equation (2), $$A \text{ correcting magnification ratio} = \frac{\text{Present SID}}{\text{Reference SID}}. \quad (2)$$

The present SID is obtained from the moving amount by the I.I. moving actuator 6a. The reference SID is a constant which is previously decided by a desired magnification of the X-ray imaging display.

By the correcting operation according to the embodiment in FIG. 6, the displayed X-ray images on the monitor 30 can maintain substantially the same magnification among them. Consequently, it becomes possible to compare a plurality of different X-ray images which have substantially the same size.

In the embodiment shown in FIG. 6, the images are processed after magnifying or reducing the images. It is also possible to process the images before the image magnification or reduction.

Further, it is possible to add the parameters relating to the rotating angle of the C-arm and the moving amounts of the C-arm and the X-ray source in the equation (2) for increasing the precision of the calculation.

As mentioned above, the X-ray examination apparatus according to the present invention can obtain good reproduced X-ray images without any complicated and difficult positioning operations of the X-ray imaging system.

What is claimed is:

1. A method for moving an image receptor in an X-ray examination apparatus which includes a movable table top, an imaging system having an X-ray source and the image receptor, an imaging system holder with a first end and a second end, wherein said imaging system holder supports said imaging system by mounting the X-ray source in said first end of said imaging system holder and supports said image receptor by mounting the image receptor in said second end of said imaging system holder, a first actuator rotating the imaging system holder about a radiation axis, a second actuator moving the image receptor along the radiation axis, and a control system for controlling a moving amount of the imaging receptor, comprising the steps of:

detecting an automatic positioning mode for moving the image receptor;

detecting a moved amount of the imaging system holder;

calculating a moving amount of the image receptor on the basis of the detected moved amount of the imaging system holder and data of the table top stored in a memory; and moving the image receptor along a radiation axis passing through the X-ray source and the image receptor by the calculated moving amount.

2. An X-ray examination apparatus comprising:

a movable table top for supporting an object being examined;

an imaging system having an X-ray source for transmitting X-rays through the object while the object is on the table top and an image receptor for generating an X-ray image of the object by detecting the X-rays transmitted through the object;

an imaging system holder with a first end and a second end, wherein said imaging system holder supports the imaging system by mounting the X-ray source in said first end of said imaging system holder and supports the image receptor by mounting the image receptor in said second end of said imaging system holder so as to dispose the table top between the X-ray source and the image receptor;

a first actuator rotating the imaging system holder to rotate a radiation axis passing between respective center portions of the X-ray source and the image receptor;

a second actuator moving the image receptor along the radiation axis; and a control system for controlling a moving amount E of the image receptor along the radiation axis by coordinating the movement of the image receptor with the movement of said imaging system holder for positioning the image receptor at a required position, wherein the control system controls movement of the image receptor in accordance with said movement of said imaging system holder and includes a memory for storing data relating to the table top, a control circuit for controlling the movement of the image receptor, a detector for detecting moved amounts of the imaging system holder, and a moving amount calculator for deciding the moving amount E of the image receptor along the radiation axis on the basis of the data in the memory and the detected moved amounts from the control circuit.

3. The X-ray examination apparatus according to claim 1, wherein the control circuit in the control system controls an automatic positioning movement of the image receptor by the second actuator when an automatic positioning mode is selected, and the moving amount calculator decides a moving amount of the image receptor along the radiation axis.

4. The X-ray examination apparatus according to claim 1, wherein the memory stores data relating to sizes of the table top and of a patient body, and the moving amount calculator selectively uses the data among the sizes of the table top and patient body for the calculation.

5. The X-ray examination apparatus according to claim 1, further comprising a control panel for the X-ray examination apparatus, and wherein the control system changes an automatic positioning mode of the image receptor and a manual positioning mode of the image receptor in response to an instruction from the control panel for the X-ray examination apparatus.

6. The X-ray examination apparatus according to claim 5, wherein the control system enters the automatic positioning mode of the image receptor when the control panel instructs an over-table-tube mode of the apparatus and releases the automatic positioning mode of the image receptor when the control panel instructs an under-table-tube mode, wherein said over-table-tube mode and under-table-tube mode correspond to the X-ray source emitting radiation from above and below the table top, respectively.

7. The X-ray examination apparatus according to claim 1 further comprising a size corrector for correcting a size of the X-ray image by magnification or reduction in response to the moving amount E of the image receptor so as to keep a constant size of the X-ray image on a monitor.

8. The X-ray examination apparatus according to claim 7, wherein the size corrector comprises:

a correcting magnification ratio calculator for deciding a magnification or reduction ratio for the X-ray image in response to an instruction from the control circuit;

means for magnifying or reducing the X-ray image under the decided magnification or reduction ratio from the correcting magnification ratio calculator; and means for processing the X-ray image for displaying on the monitor.

9. The X-ray examination apparatus according to claim 8, wherein the correcting magnification ratio calculator decides the magnification or reduction ratio by the equation $$\text{magnification or reduction ratio} = \frac{\text{Present SID}}{\text{Reference SID}}$$

where Present SID is a distance between a focusing point of the X-ray source and an image detecting surface of the image receptor, and Reference SID is a constant for obtaining a desired magnification of the X-ray image on the monitor.

10. An X-ray examination apparatus comprising:

a table top for supporting an object being examined;

an X-ray source for transmitting X-rays through said object while said object is on said table top;

an image receptor for generating an X-ray image of said object by detecting said X-rays transmitted through said object;

a holder for supporting said image receptor, wherein said holder moves said imaging receptor along a radiation axis passing between respective center portions of said X-ray source and said image receptor;

a C-shaped arm having a first end and a second end, wherein said C-shaped arm supports said X-ray source on said second end and said holder on said first end;

supporting members for supporting and moving said C-shaped arm;

a control system for controlling said holder based on a moving amount of said C-shaped arm owing to a moving amount of said supporting members so that said image receptor is positioned a predetermined distance between said table top and said imaging system holder, wherein said table top and said imaging system holder do not touch.

11. An X-ray examination apparatus comprising:

a table top for supporting an object being examined;

an imaging system having an X-ray source for transmitting X-rays through the object while the object is on the table top and an image receptor for picking-up an X-ray image passed through the object;

an imaging system holder with a first end and a second end, wherein said imaging system holder supports the imaging system by mounting the X-ray source in said first end of said imaging system holder and supports the image receptor by mounting the image receptor in said second end of said imaging system holder so as to dispose the table top between the X-ray source and the image receptor;

a plurality of holder carriages for supporting and moving the imaging system holder;

a first actuator rotating the imaging system holder about a radiation axis;

a second actuator moving the image receptor along the radiation axis; and a control system for controlling a moving amount of the image receptor by coordinating the movement of the image receptor with the movement of said imaging system holder for positioning the image receptor a minimum distance between the table top and the imaging system holder, wherein the table top and the imaging system holder do not touch, in accordance with the moving amount of the imaging system holder.

12. An X-ray examination apparatus comprising:

a movable table top for supporting an object being examined;

an imaging system having an X-ray source for transmitting X-rays through the object while the object is on the table top and an image receptor for generating an X-ray image of the object by detecting the X-rays transmitted through the object;

an imaging system holder with a first end and a second end, wherein said imaging system holder supports the imaging system by mounting the X-ray source in said first end of said imaging system holder and supports the image receptor by mounting the image receptor in said second end of said imaging system holder so as to dispose the table top between the X-ray source and the image receptor;

a first actuator rotating the imaging system holder to rotate a radiation axis passing between respective center portions of the X-ray source and the image receptor;

a second actuator moving the image receptor along the radiation axis; and a control system for controlling a moving amount E of the image receptor along the radiation axis by coordinating the movement of the image receptor with the movement of said imaging system holder for positioning the image receptor at a required position, wherein the control system controls movement of the image receptor in accordance with said movement of said imaging system holder and includes a memory for storing data relating to the table top, a control circuit for controlling the movement of the image receptor, a detector for detecting moved amounts of the imaging system holder, and a moving amount calculator for deciding the moving amount E of the image receptor along the radiation axis on the basis of the data in the memory and the detected moved amounts from the control circuit, wherein the moving amount calculator decides the moving amount E of the image receptor along the radiation axis by the equation $$E = -a \cdot \sin\theta + b \cdot \cos\theta + \frac{c}{2} \cdot |\sin\theta| + d,$$

where a is a distance between a center of said imaging system holder and a lateral center of the table top, b is a vertical distance between a surface of the table top and a rotation axis of said imaging system holder for a pitching movement passed through the center of said imaging system holder, c is a lateral width of the table top, d is a predetermined margin between a detecting surface of the image receptor and the table top, and θ is an inclined angle of the radiation axis.

13. The X-ray examination apparatus according to claim 12, wherein the memory stores data relating to sizes of the table top and of a patient body, and the moving amount calculator selectively uses the data among the sizes of the table top and patient body for the calculation.

14. The X-ray examination apparatus according to claim 12, wherein the control circuit in the control system controls an automatic positioning movement of the image receptor by the second actuator when an automatic positioning mode is selected, and the moving amount calculator decides a moving amount of the image receptor along the radiation axis.

15. The X-ray examination apparatus according to claim 12, further comprising a control panel for the X-ray examination apparatus, and wherein the control system changes an automatic positioning mode of the image receptor and a manual positioning mode of the image receptor in response to an instruction from the control panel for the X-ray examination apparatus.

16. The X-ray examination apparatus according to claim 15, wherein the control system enters the automatic positioning mode of the image receptor when the control panel instructs an over-table-tube mode of the apparatus and releases the automatic positioning mode of the image receptor when the control panel instructs an under-table-tube mode.

17. The X-ray examination apparatus according to claim 12, further comprising a size corrector for correcting a size of the X-ray image by magnification or reduction in response to the moving amount E of the image receptor so as to keep a constant size of the X-ray image on a monitor.

18. The X-ray examination apparatus according to claim 17, wherein the size corrector comprises:
- a correcting magnification ratio calculator for deciding a magnification or reduction ratio for the X-ray image in response to an instruction from the control circuit;
- means for magnifying or reducing the X-ray image under the decided magnification or reduction ratio from the correcting magnification ratio calculator; and
- means for processing the X-ray image for displaying on the monitor.

19. The X-ray examination apparatus according to claim 18, wherein the correcting magnification ratio calculator decides the magnification or reduction ratio by the equation $$\text{magnification or reduction ratio} = \frac{\text{Present SID}}{\text{Reference SID}},$$

where Present SID is a distance between a focusing point of the X-ray source and an image detecting surface of the image receptor, and Reference SID is a constant for obtaining a desired magnification of the X-ray image on the monitor.

* * * * *